United States Patent

Ouchi

[11] Patent Number: 6,083,240
[45] Date of Patent: Jul. 4, 2000

[54] LINK MECHANISM UNIT INCLUDED IN A LINK MECHANISM FOR AN ENDOSCOPIC FORCEPS

[75] Inventor: Teruo Ouchi, Tokyo, Japan

[73] Assignee: Asahi Kogaku Kogyo Kabushiki Kaisha, Tokyo, Japan

[21] Appl. No.: 09/013,263

[22] Filed: Jan. 26, 1998

[30] Foreign Application Priority Data

Jan. 29, 1997 [JP] Japan .................................... 9-014992

[51] Int. Cl.[7] ..................................................... A61B 17/28
[52] U.S. Cl. .............................................................. 606/205
[58] Field of Search ..................... 606/205–207, 606/208, 209; 30/186, 188, 266; 81/418, 422

[56] References Cited

U.S. PATENT DOCUMENTS 4,669,471  6/1987  Hayashi .
5,681,348  10/1997  Sato ........................................ 606/205

Primary Examiner—Michael Buiz
Assistant Examiner—Vikki Trinh
Attorney, Agent, or Firm—Greenblum & Bernstein, P.L.C.

[57] ABSTRACT

A link mechanism unit of an endoscopic forceps is assembled by riveting an end of a coupling pin so that the link mechanism can be smoothly moved without unpleasant resistance. A coupling pin insertion hole is opened so as to pass through overlapping links;, and a counterbore is formed in a mouth portion of the coupling pin insertion hole. When the head of a coupling pin passed through the coupling pin insertion hole abuts against the counterbore, the end face of the head of the coupling pin is positioned to be inwardly recessed from an outer open end face of the counterbore.

4 Claims, 5 Drawing Sheets

LINK MECHANISM UNIT INCLUDED IN A LINK MECHANISM FOR AN ENDOSCOPIC FORCEPS

BACKGROUND OF THE INVENTION

The invention relates to a link mechanism unit included in a link mechanism for an endoscopic forceps in which forceps cups are mutually opened and closed by remotely operating the link mechanism disposed on the side of the distal end.

Generally, a link mechanism unit of an endoscopic forceps is assembled such that plural links constituting a link mechanism overlap with each other in a link coupling portion, and then coupled to one another such that a coupling pin is welded to links by laser welding or the like. However, a laser welding apparatus is expensive and hence it is often that such an apparatus cannot be used in a usual production process.

SUMMARY OF THE INVENTION

Therefore, it is an object of the invention to provide a link mechanism unit of an endoscopic forceps, which can be assembled by simply riveting an end of a coupling pin to prevent removal of the coupling pin from a coupling pin insertion hole, and which can permit the smooth movement of a link mechanism without unpleasant resistance.

In order to attain the object, the invention provides a novel link mechanism unit included in a link mechanism for an endoscopic forceps in which forceps cups coupled to the link mechanism are mutually opened and closed by remotely operating the link mechanism. The link mechanism unit includes: at least two links overlapping with each other in a link coupling portion; a coupling pin insertion hole opened in the link coupling portion to pass through the at least two links; a counterbore formed in a mouth portion of the coupling pin insertion hole; and a coupling pin passed through the coupling pin insertion hole and rotatably supporting the at least two links. The coupling pin is provided, at its one end, with a head substantially corresponding in shape to the counterbore, and at its the other end with a riveted portion. Under a state where the head of the coupling pin abuts against the counterbore of the coupling pin insertion hole, an end face of the head of the coupling pin is positioned with being inwardly recessed from an outer open end face of the counterbore.

The link mechanism unit of the invention can be applied to endoscopic forceps of various kinds, including a biopsy forceps and a grasping forceps.

The end face of the head of the coupling pin may be recessed from the outer open end face of the counterbore by 0.02 to 0.2 mm.

The counterbore may have a conical shape or a cylindrical shape.

The invention further provides a process for forming a link mechanism unit included in an endoscopic forceps link mechanism. The process includes the steps of: positioning at least two links to define a coupling pin insertion hole passing through the at least two links at a link coupling portion; inserting a coupling pin into the coupling pin insertion hole so that a head provided at one end of the coupling pin is located in a counterbore formed in a mouth portion of the coupling pin insertion hole while the other end of the coupling pin is projected from the coupling pin insertion hole; placing the at least two links with the coupling pin inserted therein onto a table so that both an end face of the head and an outer open end face of the counterbore contact the table while the head is spaced from the counterbore; and riveting the other end of the coupling pin to couple the at least two links by the coupling pin.

According to the invention, a coupling pin insertion hole is opened so as to pass through overlapping links, a counterbore is formed in a mouth portion of the coupling pin insertion hole, and, under a state where the head of the coupling pin passed through the coupling pin insertion hole abuts against the counterbore, the end face of the head of the coupling pin is positioned with being inwardly recessed from an outer open end face of the counterbore. When the other end of the coupling pin which is opposite to the head is riveted, therefore, the coupling pin is not firmly fixed to the coupling pin insertion hole. Even when lapping or the like is not conducted thereafter, the link mechanism smoothly operates without unpleasant resistance.

The present disclosure relates to the subject matter contained in Japanese patent application No. 9-14992 filed on Jan. 29, 1997, which is expressly incorporated herein by reference in its entirety.

DETAILED DESCRIPTION OF LINK MECHANISM UNIT

Figure 9:
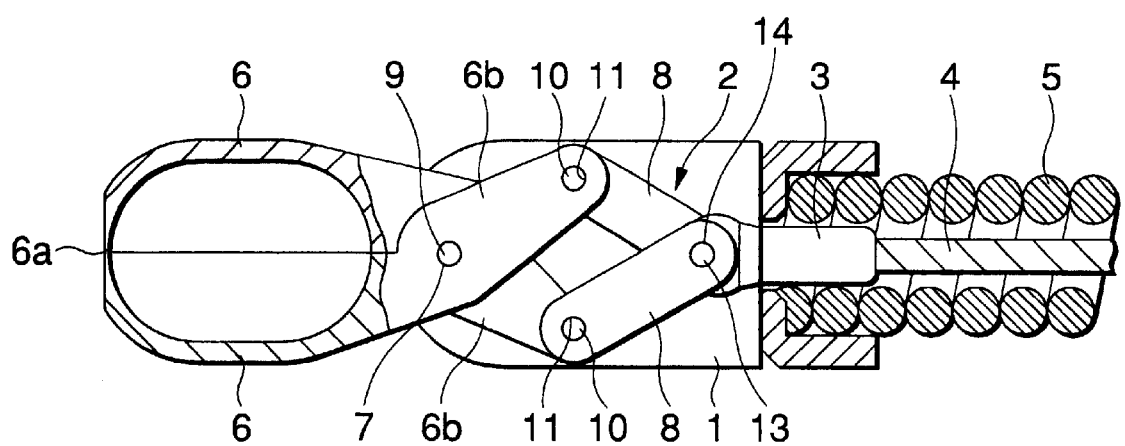
FIG. 9 is a side section view of a distal end portion of an endoscopic biopsy forceps.

FIG. 9 shows a distal end portion of an endoscopic biopsy forceps.

In FIG. 9, 1 designates a support member in the form of a metal bar, which is rounded in section with a slit axially elongated from one end thereof. A link mechanism 2 is disposed inside the slit of the support member 1.

The reference numeral 5 designates a flexible sheath which is formed by, for example, tightly winding a stainless steel wire into a coil-like shape. An operating wire 4 is advanceably and retreatably passed through the flexible sheath 5. One end of the operating wire 4 is coupled to the link mechanism 2 via a joint 3, and the other end of the operating wire 4 is coupled to an operating unit not shown in the drawings.

A pair of forceps cups 6 have blades 6a formed on outer edge portions. A link piece 6b is formed in a rear portion (proximal end) of each of the forceps cups 6. The link pieces 6b are rotatably supported on the support member 1 by a first coupling pin 9.

A coupling pin insertion hole 7 is opened in an area where the link pieces 6b of the pair of forceps cups 6 and the support member 1 disposed on either side of the link pieces 6b overlap with each other, so as to pass through these components orthogonally. The forceps cups 6 are rotatably supported by the first coupling pin 9 which is passed through the coupling pin insertion hole 7.

The proximal ends of the link pieces 6b of the pair of forceps cups 6 are coupled to link plates 8 by second coupling pins 10, respectively. The second coupling pins 10 are passed through coupling pin insertion holes 11 which are opened, in parallel to the hole 7, in areas where the link pieces 6b of the forceps cups 6 and the link plates 8 overlap with each other, respectively. The link plates 8 are rotatable about the respective second coupling pins 10.

The proximal ends of the two link plates 8 are rotatably coupled to the joint 3 by a third coupling pin 13. A coupling pin insertion hole 14 is opened, in parallel to the hole 7, in an area where the two link plates 8 overlap with each other with placing the joint 3 therebetween. The third coupling pin 13 is passed through the hole 14.

Figure 1:
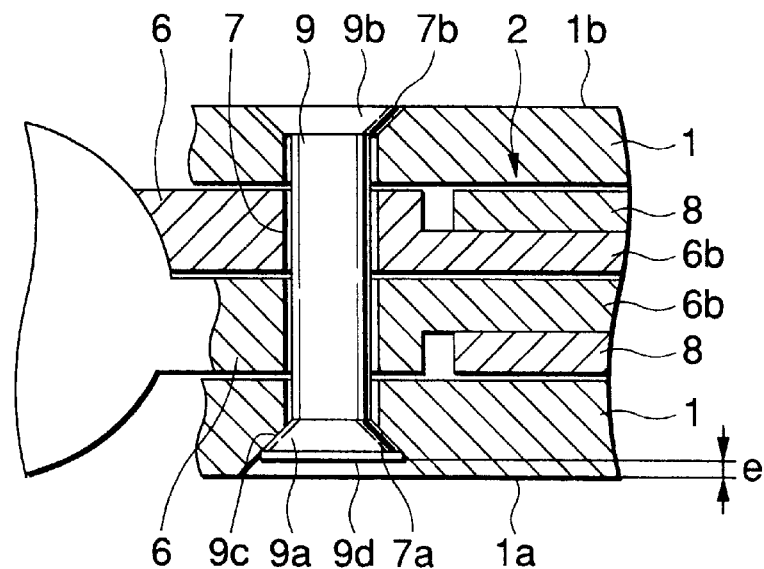
FIG. 1 is an enlarged partial sectional view of a link mechanism unit.

FIG. 1 shows a section of the area where the pair of forceps cups 6 are supported on the support member 1 by the first coupling pin 9. Counterbores 7a and 7b which are taper-chamfered or conical are formed in the mouth portions of the coupling pin insertion hole 7 which are formed in the outer face of the support member 1, respectively.

A dish-like (tapered or conical) head 9a which makes a close contact with the counterbore 7a of the coupling pin insertion hole 7 is formed at one end of the first coupling pin 9 which is loosely inserted through the coupling pin insertion hole 7.

Under the state where the tapered face 9c of the head 9a of the first coupling pin 9 makes close contact with that of the counterbore 7a, the planar surface 9d of the head 9a of the first coupling pin 9 is positioned inwardly recessed from the surface 1a of the support member 1 (i.e., the outer open end face of the counterbore 7a). The tapered surface of the counterebore 7a is analogous in configuration to the tapered surface 9c of the head 9a. The recession amount e is in the range of 0.02 to 0.2 mm.

The other end 9b of the first coupling pin 9 is collapsed by riveting so as to fill the counterbore 7b on the side of the other end of the first coupling pin 9. Thereafter, the surface of the other end is ground with a fine file or the like so as to be flush with the surface 1b of the support member 1.

Figure 2:
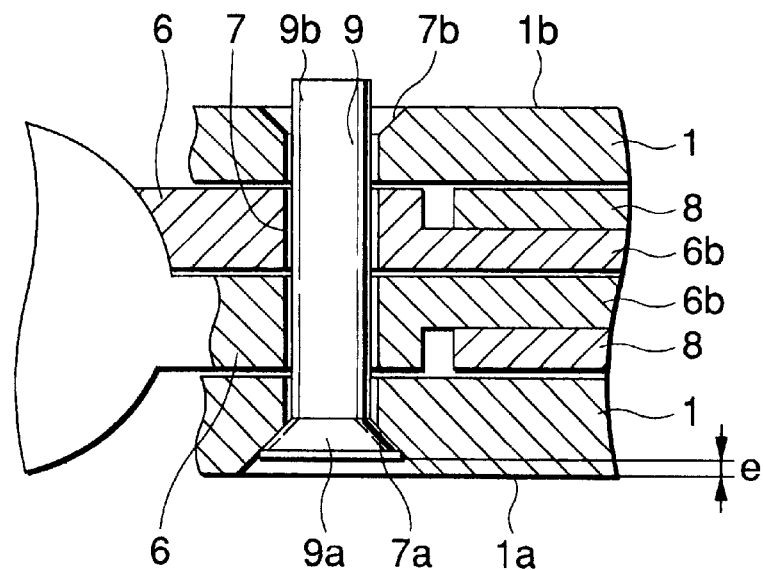
FIG. 2 is an enlarged partial sectional view of the link mechanism unit before a riveting process.
Figure 3:
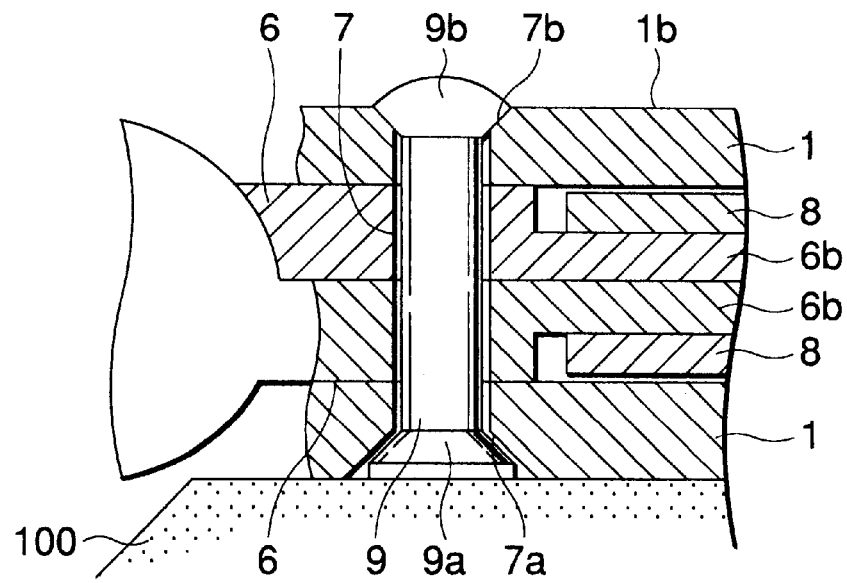
FIG. 3 is an enlarged partial sectional view of the link mechanism unit during the riveting process.
Figure 4:
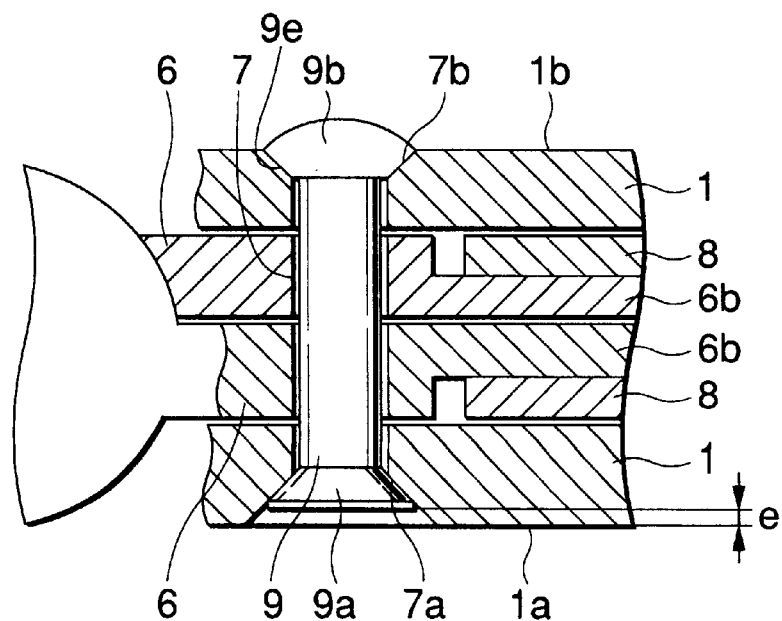
FIG. 4 is an enlarged partial sectional view of the link mechanism unit after the riveting process.

FIGS. 2 to 4 show steps which are conducted before and after the process of riveting the first coupling pin 9. As shown in FIG. 2, before the riveting process, all the portions of the first coupling pin 9 other than the head 9a have a columnar shape having a uniform diameter, and the other end 9b which is opposite to the head 9a is passed through the coupling pin insertion hole 7 to be projected from the outer face of the support member 1.

As shown in FIG. 3, the link assembly is placed on a rivet table 100 with the head 9a of the first coupling pin 9 positioned downward, and under this state the other end 9b of the first coupling pin 9 is beaten with a hammer or the like so as to be collapsed by a riveting process.

At this time, the force exerted by the riveting process causes the support member 1 to be elastically deformed, so that the pair of forceps cups 6 and the support member 1 disposed so as to sandwich the cups 6 make close contact with each other and the surface 9d of the head 9a of the first coupling pin 9 abuts against the rivet table 100. As a result, a gap is formed between the tapered face 9c of the head 9a of the first coupling pin 9 and that of the counterbore 7a, and hence the first coupling pin 9 is not fixed into the coupling pin insertion hole 7.

When the riveting process is ended, the support member 1 is returned to the original state by its own elasticity. As shown in FIG. 4, therefore, both the tapered faces 9c, 9e of the head 9a and the other end 9b of the first coupling pin 9 abut against the tapered faces of the counterbores 7a and 7b, respectively.

A small gap (about one third of e) is formed between adjacent ones of the support member 1 and the link pieces 6b of the two forceps cups 6. Consequently, the friction produced between the contacting faces of the adjacent ones of the member and the pieces are reduced, so that smooth movement without backlash can be attained. Finally, the projection of the riveted portion of the other end 9b of the first coupling pin 9 is ground away, so that the finished state shown in FIG. 1 is attained.

Figure 5:
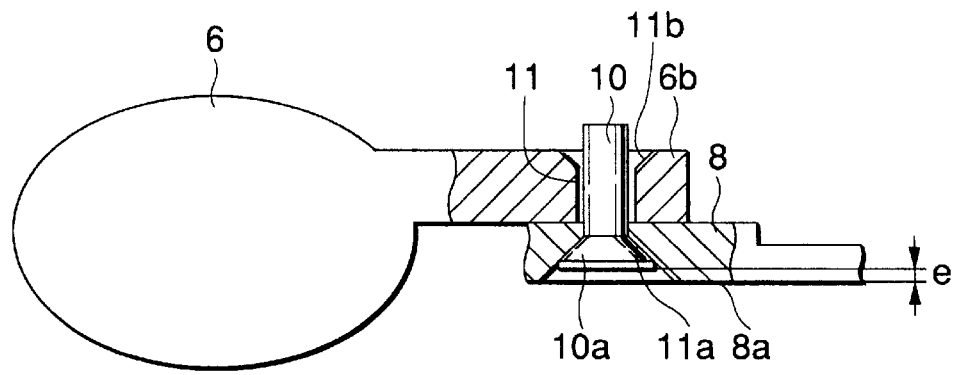
FIG. 5 is an enlarged partial sectional view of another link mechanism unit before a riveting process.
Figure 6:
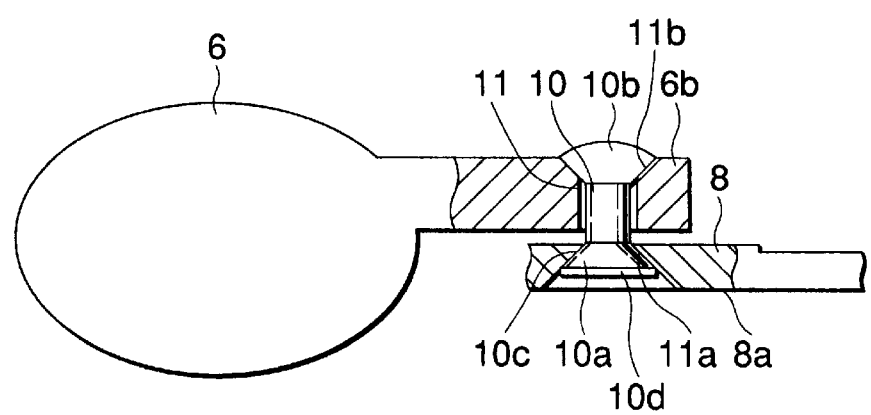
FIG. 6 is an enlarged partial sectional view of the link mechanism unit shown in FIG. 5 after the riveting process.

FIGS. 5 and 6 show steps of a riveting process for another link mechanism unit, which is arranged in the coupling portion between the link piece 6b of the forceps cup 6 and the link plate 8.

In the coupling portion, the link piece 6b of the forceps cup 6 and the link plate 8 overlap with each other, and the second coupling pin 10 which is shorter than the coupling pin 9 is passed through a coupling pin insertion hole 11 and then riveted. The reference numerals 11a and 11b designate tapered counterbores formed in the mouth portions of the coupling pin insertion hole 11.

Under the state where the tapered face 10c of the head 10a of the second coupling pin 10 makes close contact with that of the counterbore 11a, the surface 10d of the head 10a of the second coupling pin 10 is positioned with being inwardly recessed from the surface 8a of the link plate 8 (i.e., the outer open end face of the counterbore 11a).

The other configurations such as that the recession amount e is in the range of 0.02 to 0.2 mm, and that the other end 10b of the second coupling pin 10 which is opposite to the head 10a is riveted as shown in FIG. 6 and then ground so as to be flush with the surface of the link piece 6b of the forceps cup 6 are identical with those of the coupling portion shown in FIGS. 1 to 4.

Figure 7:
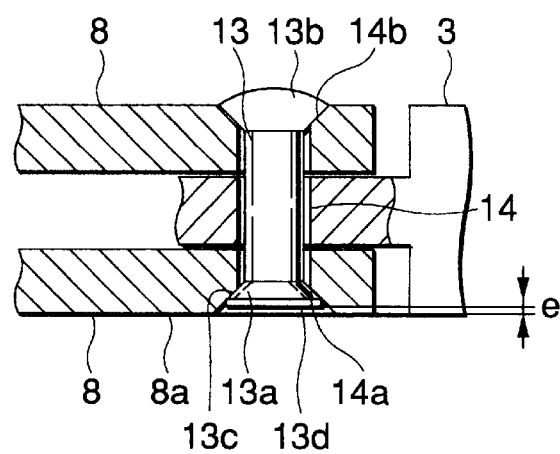
FIG. 7 is an enlarged partial sectional view of another link mechanism unit after the riveting process.

FIG. 7 shows a state where a riveting process is conducted for the coupling portion between the joint 3 to which the operating wire 4 is coupled and the two link plates 8 which interpose the point therebetween. The reference numeral 14 designates a coupling pin insertion hole, and 14a and 14b designate tapered counterbores formed in the mouth portions of the hole.

The configurations such as that, under the state where the tapered face 13c of the head 13a of the third coupling pin 13 makes close contact with that of the counterbore 14a, the recession amount e of the surface 13d of the head 13a of the third coupling pin 13 from the surface 8a of the link plate 8 (i.e., the outer open end face of the counterbore 14a) is in the range of 0.02 to 0.2 mm, and that the other end 13b of the third coupling pin 13 which is opposite to the head 13a is riveted as shown in FIG. 7 and then ground so as to be flush with the surface of the link plate 8 are identical with those of the coupling portions shown in FIGS. 1 to 6.

Figure 8:
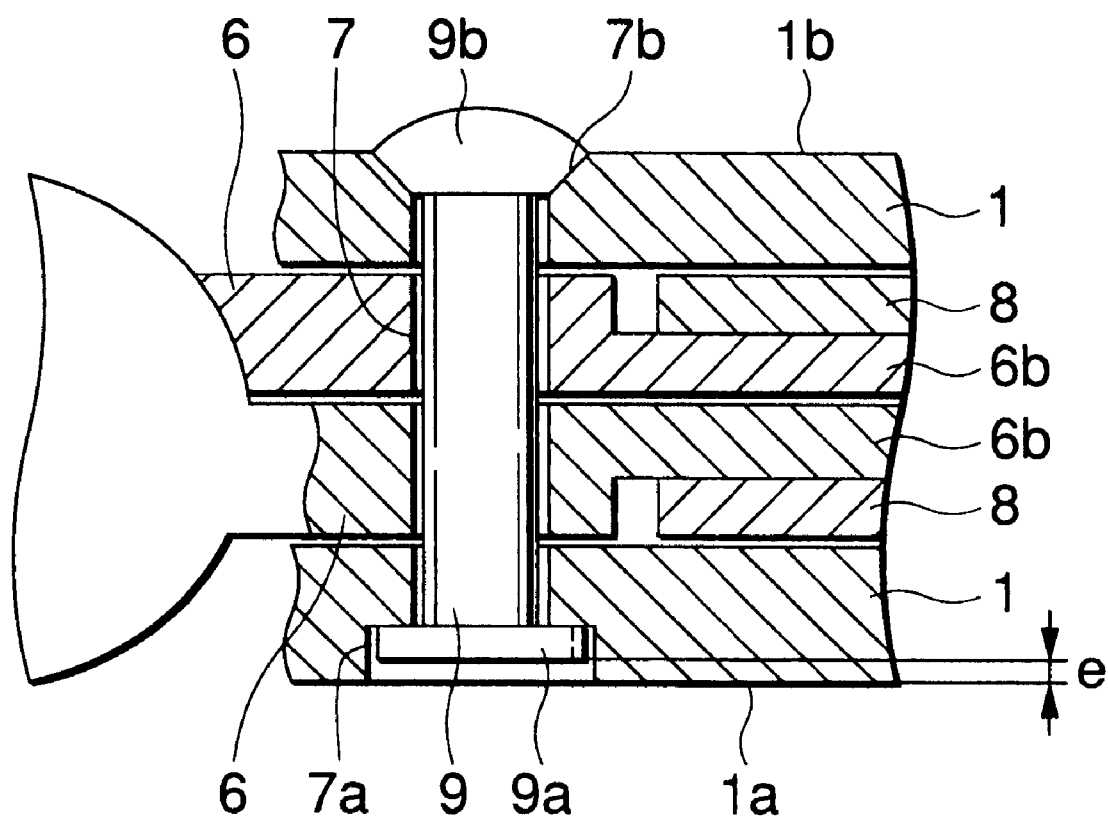
FIG. 8 is an enlarged partial sectional view of another link mechanism unit after the riveting process.

FIG. 8 shows a modification for the coupling portion, wherein the counterbore 7a of the coupling pin insertion hole 7 into which the head 9a of the first coupling pin 9 is fitted is formed as a so-called cylindrical counterbore which does not have a conical shape but has a cylindrical shape. The head 9a is also cylindrical, not tapered. The other configurations are identical with those of the coupling portion shown in FIGS. 1 to 4.

What is claimed is:

1. A process for forming a link mechanism unit included in an endoscopic forceps link mechanism, said process comprising:

positioning at least two links to define a coupling pin insertion hole passing through said at least two links at a link coupling portion;

inserting a coupling pin into said coupling pin insertion hole so that a head provided at one end of said coupling pin is located in a counterbore formed in a mouth portion of said coupling pin insertion hole while the other end of said coupling pin is projected from said coupling pin insertion hole;

placing said at least two links with said coupling pin inserted therein onto a table so that both an end face of said head and an outer open end face of said counterbore contact said table while said head is spaced from said counterbore; and riveting said other end of said coupling pin to couple said at least two links by said coupling pin, so that said end face of said head is positioned inwardly recessed from said outer open end face of said counterbore.

2. A process for forming a link mechanism unit according to claim 1, further comprising:

grinding said the other end of said coupling pin thus riveted to be flush with an outer surface of said at least two links.

3. A link mechanism unit included in a link mechanism for an endoscope forceps, in which a pair of forceps cups coupled to said link mechanism are mutually opened and closed by remotely operating said link mechanism, said link mechanism unit comprising:

at least two links overlapping each other in a link coupling portion;

a coupling pin insertion hole opened in said link coupling portion to pass through said at least two links;

a counterbore having a predetermined depth formed in a mouth portion of said coupling pin insertion hole; and a coupling pin passed through said coupling pin insertion hole and rotatably supporting said at least two links, said coupling pin provided, at its one end, with a head substantially corresponding in shape to said counterbore, said head having a predetermined length, said predetermined depth of said counterbore being larger than a predetermined length of said head, and a riveted portion provided at the other end of said coupling pin, wherein when said head of said coupling pin abuts against said counterbore of said coupling pin insertion hole, said head of said coupling pin is positioned inwardly recessed from an outer open end face of said counterbore and a distance between an end face of said head of said coupling pin and said outer open end face of said counterbore being 0.02 to 0.2 mm.

4. A link mechanism unit according to claim 3, wherein said counterbore has a cylindrical shape.

* * * * *